United States Patent [19]

Herman

[11] Patent Number: 4,983,637

[45] Date of Patent: Jan. 8, 1991

[54] METHOD FOR TREATING VIRAL INFECTION OF HIV

[76] Inventor: Stephen Herman, 9341 Hazel Cir., Villa Park, Calif. 92667

[21] Appl. No.: 363,628

[22] Filed: Jun. 8, 1989

Related U.S. Application Data

[63] Continuation-in-part of Ser. No. 211,378, Jun. 24, 1989, abandoned.

[51] Int. Cl.$^5$ .................... A01N 31/00; A01N 31/04; A61K 31/045; A61K 31/07
[52] U.S. Cl. .................................. 514/724; 514/725; 514/739
[58] Field of Search .............. 549/430, 431, 347, 357, 549/510; 568/448, 461, 469, 486, 590, 840, 875, 909.5; 560/205; 514/724, 725, 739

[56] References Cited

U.S. PATENT DOCUMENTS

| | | | |
|---|---|---|---|
| 925,590 | 6/1909 | Neel | 549/431 |
| 1,210,949 | 1/1917 | Knox | 549/431 |
| 1,910,564 | 5/1933 | Rankin | 549/431 |
| 2,083,572 | 6/1937 | McKee | 549/431 |
| 2,243,053 | 5/1941 | Ramage | 549/431 |
| 2,356,062 | 8/1944 | Johnson | 260/410.7 |
| 2,750,411 | 6/1956 | Fisher et al. | 549/431 |
| 3,360,472 | 12/1967 | Renold | 549/431 |
| 3,504,038 | 3/1970 | Beal | 568/469 |
| 4,451,480 | 5/1984 | De Villez | 424/278 |
| 4,591,602 | 5/1986 | De Villez | 514/463 |
| 4,632,980 | 12/1986 | Zee et al. | 530/380 |

OTHER PUBLICATIONS

Russell-Manning, editor, "Self-Treatment for AIDS, Oxygen Therapies, etc., " Greensward Press, San Francisco, 1988, 1989, pp. 22-27.

P. Bailey et al., "Complexes and Radicals Produced During Oxonation of Olefins", Ozone Reactions with Organic Compounds, Advances in Chemistry, Series 112, pp. 1-8 (1972).

*Primary Examiner*—Nathan M. Nutter
*Attorney, Agent, or Firm*—Knobbe, Martens, Olson & Bear

[57] ABSTRACT

Methods of treating systemic viral infections are disclosed comprising the parenteral administration of pharmacologically effective amounts of ozonides of terpenes in pharmaceutically acceptable carriers. Methods for treating viral lesions are also disclosed. In particular, a method for treating rfetroviral infections is disclosed. More particularly, a method for treating HIV infections is disclosed. In addition, methods for treating infections of non-retroviral viruses are disclosed. Further, methods for trating T-cell deficiencies are also disclosed. Moreover, a method of producing blood for medical products which is free of viral activity is disclosed.

8 Claims, No Drawings

METHOD FOR TREATING VIRAL INFECTION OF HIV

CROSS REFERENCE TO RELATED APPLICATION

This application is a continuation-in-part of U.S. application Ser. No. 211,378, filed June 24, 1988.

This invention relates to methods of medical treatment. More particularly, it relates to the use of ozonides of terpene hydrocarbons in the treatment of viral infections and certain immune disorders.

BACKGROUND OF THE INVENTION

Methods of medical treatment employing ozonides of oil-soluble compounds are known in the being disclosed, for example, in U.S. Pat. No. 925,590 to Neel, U.S. Pat. No. 2,083,572 to McKee, and U.S. Pat. No. 4,451,480 to De Villez.

The prior art does not disclose the use of ozonized compounds as an antiviral or immunotherapeutic agent. However, particular types of ozonide structures have been disclosed to have certain pharmacological activity In U.S. Pat. No. 925,590, Neel reports the use of ozonides of terpenes and other ozonides for inhalation therapy, because it was believed to have a therapeutic effect for consumption and asthma. Although the Neel patent application was filed in 1902, there have apparently been no supporting data reported in the intervening years that corroborate the utility theorized by Neel.

Knox, U.S. Pat. No. 1,210,949 discloses use of ozonized castor oil as a laxative. Ozonation of the oil was believed to reduce its toxicity and create a germicidal effect.

Johnson, U.S. Pat. No. 2,356,062 discloses the use of ozonides of glycerine trioleates for external application, because it was believed that those particular triglycerides had a germicidal, fungicidal and deodorizing effect.

De Villez, U.S. Pat. Nos. 4,451,480 and 4,591,602, discloses use of ozonides or certain fatty acids, including olive oil, sesame oil, jojoba oil, castor oil and peanut oil, for external use as antimicrobial agents, particularly in the treatment of acne. It is believed that at least some of these compounds cause unacceptable skin irritation.

So far as can be determined, none of the medical uses of ozonides described in the prior art have ever been commercialized. Presumably, this lack of commercialization is due to unacceptable side-effects, toxicity, difficulties in storage, or minimal effectiveness. Many of these various compositions decompose on standing. Also, to the extent that the mechanism of action of these compositions can be attributed to their oxygen content, most of the ozonides known in the prior art have been suboptimal because these compounds typically release no more than about 18% of their weight as oxygen.

Methods of medical treatment employing antiviral compounds are known in the art. Most of the research in this area has focused on nucleoside analogues. Dideoxynucleosides are antiviral nucleoside analogues which are useful in treating retroviral infections where viral replication requires the transcription of viral RNA into DNA by viral reverse transcriptase. Other nucleoside analogues include deoxynucleosides and nucleoside analogues, such as acyclovir and gancyclovir which have only a fragment of ribose or other pentose connected to the base molecule. Nucleoside analogues have been shown to be only minimally effective in the treatment of viral infections that are not caused by retroviruses.

Antiviral agents other than nucleoside analogues are also known. For example, amantadine is an antiviral agent that prevents binding of certain viruses with their receptor on the cell surface. However, amantadine is ineffective against many known viruses.

Acquired immunodeficiency syndrome (AIDS) is a fatal condition caused by the human immunodeficiency virus (HIV), a retrovirus. Since AIDS was identified as a medical condition in 1981, over 100,000 cases have been reported worldwide, with over half of these cases in the United States. It is believed that over 2,000,000 people worldwide are carriers of the HIV virus, with infections continuing to spread. Researchers now believe that most of these carriers will one day develop symptoms of AIDS. No effective cure is available for AIDS, although dideoxynucleosides and their analogues have been shown to prolong life and to reduce the incidence of certain fatal infections associated with AIDS. Among the dideoxynucleoside analogues, AZT has shown the most promise as a treatment for AIDS. However, treatment of AIDS patients with AZT has proven to be of only poor to moderate effectiveness, and AZT does not cure AIDS. Moreover, in a recent human trial, serious toxicity was noted, evidenced by anemia (24%) and granulocytopenia (16%). Clearly, there is a tremendous need for a non-toxic and effective treatment for HIV infection.

It is believed that HIV causes AIDS, in part, by infecting helper/inducer T4-cells and causing a T4-cell deficiency. Other conditions may also cause this deficiency, including immunosuppressive therapy for transplant patients, radio-therapy or chemotherapy in cancer patients, and congenital immunodeficiencies. Current immune boosting therapies, such as the use of interleukin-2 or $\gamma$-interferon are still in the experimental stages, and have not yet been proven effective. No proven effective treatments are currently in use for restoring a normal level of T-cells. Thus, a need exists for such a treatment.

Transmission of HIV through blood products has been shown to occur. The discovery of the HIV antibody test, and its application to blood products prior to release has reduced the incidence of transmission through blood products. However, the HIV antibody test is not 100% effective in detecting the presence of HIV virus particles, in part, because an infected individual may not produce antibodies to HIV for six months or longer after infection. There is, therefore, still a low incidence of blood products tainted with HIV being released for medical use. Moreover, blood products may be tainted with other viruses capable of being transmitted through the blood, such as Hepatitis B. A method of treating blood products to eliminate viral activity without affecting their efficacy in treatments is highly desireable.

Retroviruses other than HIV are known. These include the herpes family of viruses, HTLV I, and cytomegalovirus (CMV). Infections of these viruses have been notoriously difficult to treat. No vaccines are known for these infections. Although acyclovir has been used in the treatment of Herpes lesions, toxic side effects are known, and such treatment is not always effective. Thus, a need exists for non-toxic and effective treatments.

Human papilloma viruses are nonretroviral viruses responsible for warts of the skin or mucous membranes.

Common warts are found in as many as 25% of some groups, and are most prevalent among children. Moreover, the incidence of venereal warts (condylomata acuminata and molluscum contageosum) has risen dramatically in the last few years, to the point that this condition is one of the most common sexually transmitted diseases in the United States. Common treatments for warts are often painful and invasive, and involve physical removal of the lesion through application of caustic agents, cryosurgery, electrodessication, surgical excision, or ablation with laser. Treatment with nucleoside analogues or interferon is also sometimes used. However, no treatment of proven safety and efficacy is currently available for warts Furthermore, at the present time, no effective methods of prevention are available for warts other than avoiding contact with infectious lesions. Therefore, a need exists for a method of treatment and prevention of warts.

Other nonretroviral viruses are responsible for many of the known infections in mammals. Vaccines are known for a minority of these infections. Measles, rubella, polio, rabies, certain strains of influenza, and mumps are examples of infections caused by viruses for which vaccines are known. However, the existence of a vaccine does not obviate the need for treatment of individuals already infected. Most other viruses, including Epstein Barr Virus, and most of the enteroviruses, reoviruses, rhabdoviruses other than rabies, arboviruses, and arenaviruses produce infections for which no vaccines are known. Currently used antiviral treatments for infections of these viruses include application of nucleoside analogues or amantadine, and various interferon treatments. Unfortunately, use of these treatments is of minimal or no effectiveness against infections of most of these viruses. The use of currently known antiviral compounds is, at best, moderately effective. Moreover, toxic side-effects are common. Thus a need exists for a wide-spectrum antiviral agent that is both non-toxic and effective.

Virtually all humans occasionally suffer from upper respiratory infections, such as colds and flu. The symptoms of these infections include sore throat, runny nose, itchy eyes, and earache. In addition to these discomforts, the infections are responsible for many days of absence from work and contribute to a decrease in worker efficiency. These infections are caused by a wide variety of viruses. Although vaccines are known for a minority of flu strains, no effective methods of prevention are known for most upper respiratory infections, and no truly effective methods of treatment are known for any of these infections. A method of treating these symptoms and underlying infections would be of tremendous benefit.

Moreover, there are a number of ailments that may or may not be of viral origin, for which no effective treatments are widely available. Epstein-Barr virus (EBV) is the causative agent in infectious mononucleosis, and has been implicated in chronic fatigue syndrome. Many autoimmune disorders, such as systemic lupus erythematosis and rheumatoid arthritis, may be associated with a virus. Whether or not these diseases are of viral origin, however, they are debilitating ailments for which an effective therapy would be of major importance.

Finally, there are a number of situations, both in research and in medicine, in which generation of the superoxide radical, $O_2^-$, is advantageous. Superoxide is commonly generated through the use of xanthine oxidase acting on xanthine. However, these materials are relatively expensive and are not particularly suited for many utilities, including in vivo utilities. Thus, a method for generating superoxide that is safe and inexpensive would be advantageous.

SUMMARY OF THE INVENTION

According to the invention, there are provided novel methods of treatment and prevention of systemic and local viral infections. Methods for treating nonretroviral and retroviral infections in particular are also provided. More particularly, a method for treating retroviral HIV infections is provided. Moreover, the invention provides a method of treating blood products which removes any viral activity present in the blood. Additionally, the invention provides a method of treating immunosuppression characterized by T-cell deficiencies.

The invention, in addition, provides pharmaceutical compositions for use in the above novel treatments, containing ozonides of terpenes and a pharmaceutically acceptable carrier, and may contain other active ingredients. Preferably, these compositions are in dosage form comprising a clinically effective amount of the active compound. In one preferred embodiment of the invention, the pharmaceutical composition is comprised of an ozonized terpene in a stable injectable composition. In other preferred embodiments, the pharmaceutical compositions are in the form of nosedrops or nasal sprays, inhalants, throat sprays, eardrops, ophthalmic ointments or drops, vaginal or rectal suppositories, or ointments or creams for topical applications.

Moreover, the present invention includes the use of terpene ozonides and other ozonides of unsaturated hydrocarbons to treat autoimmune disorders, and to produce superoxide radical upon combination with an aqueous system.

DETAILED DESCRIPTION OF THE INVENTION

Terpene hydrocarbons are also known as isoprenoids, because they may generally be constructed from isoprene units. Terpene hydrocarbons are usually exact multiples of $C_5H_8$. Terpenes are classified according to the number of isoprene units of which they are composed, as shown in Table 1.

TABLE 1

| 1 hemi- | 5 ses- |
| 2 mono- | 6 tri- |
| 3 sesqui- | 8 tetra- |
| 4 di- | n poly- |

While not limiting the scope of the invention, examples of terpenes which may prove especially effective, when used in the method of the preferred embodiment, include limonene, citronella, alpha-carotene, beta-carotene, Vitamin A, geraniol, linalool, linalyl acetate, and squalene. Other compounds which are believed to make pharmacologically active terpene ozonides in accordance with the present invention include limonene, alpha-pinene, loganin, cymene, farnesanes, eudesmanes, acoranes, cedranes, chamigranes, caryophyllanes, illudanes, humulenes, himachalenes, longifolanes, perhydroazulenes, quaianes, quaianolides, and germacranes. Still other compounds which are believed to make pharmacologically active terpene ozonides in accordance with the present invention include labdanes, clerodanes, abietic acid, phyllocladene, giberellins, ophiobolin A, retigeranic acid, gasgardic acid, lanosterol, euphol, oleanane, ursane, lupeol, hydroxyhopanone, lupanes, and hopanes. Other particular terpene compounds which are believed to make pharmacologically active terpene ozonides when prepared in accordance with the present invention include B-selinene, zingibene, camphene, sabinene, ocimene, myrcene, nerol, citral A, citral B, farnesol, bisabolene, phytol, and cecropia hormone. Citral, geraniol, and nerol are particularly preferred terpenes. Ozonides of terpenes have three oxygen atoms replacing the double bonds at sites of unsaturation, creating a trioxyacyclopentane.

In the preparation of terpene ozonides, the particular desired terpene starting material is first obtained. A large and representative number of such terpenes are disclosed in the literature and/or are commercially available. (Many terpenes are essential oils that have been isolated from various parts of plants or wood by steam distillation or extraction.)

In the ozonide synthesis, ozone is passed through the terpene under conditions that provide for intimate contact between the terpene starting material and the ozone, such as thin film procedures, sparging, gas entrainment procedures, and the like. On a small scale, for example, the terpene is placed in a vented vessel, and ozone is sparged through the material until the reaction is complete. The ozone may advantageously be generated with any of the commercially-available ozone generators. Such devices include corona discharge tubes through which oxygen gas may be passed. For example, pure oxygen gas passing through an ozone generator will typically leave the device as from 2% to 6% $O_3$ (ozone), with the remainder $O_2$. This ozone mixture may then be sparged through the terpene at ambient temperature and pressure until the reaction is complete. Completion may be judged by analyzing the gas exiting the ozonation chamber for ozone. (This may be done by passing the exit gas through aqueous potassium iodide and determining whether iodine gas is liberated, or by any other conventional technique.) Alternatively, the reaction may be followed by observing the weight gain of the material undergoing the reaction, by observing changes in physical characteristics (such as conversion from a liquid form to a soft paste), or by simply calculating the quantity of ozone needed to fully ozonate the material and stopping the reaction when a slight excess of ozone has passed through the reaction chamber. Because the reaction is exothermic, its progress may also be followed by monitoring the heat evolved by the reaction medium, and stopping the flow of ozone when the mixture ceases to generate heat.

When the terpene is normally a solid, such as $\beta$-carotene, it may be solubilized in any suitable saturated nonaqueous solvent system prior to ozonation. With all of the terpene ozonides, it is desirable to exclude water, lower alcohols, nucleophilic peroxides, and proton donors from the reaction mixture and from the final composition, in order to prevent premature hydrolysis of the trioxolane ring.

Other suitable ozonation procedures may be used, such as the procedures disclosed in U.S. Pat. Nos. 2,083,572, 3,504,038, and 4,451,480.

In certain preferred embodiments of the present invention, the terpene ozonides are formulated into pharmaceutical preparations. These pharmaceutical preparations include one or more terpene ozonides, and may further include other pharmaceutically active ingredients. In addition, any of the well-known pharmaceutically-acceptable carriers or excipients may be combined with terpene ozonides in a well-known manner. Suitable diluents include, for example, polyethylene glycol, DMSO, isopropyl myristate, and mineral oil. Conventional coloring, fragrance, and preserving agents may also be provided.

It is believed that the excellent weight to oxygen ratio of some of the terpene ozonides renders them especially effective as antiviral agents. Some of the terpene ozonides are capable of releasing large amounts of oxygen, up to 30% of the weight of the compound. This is because terpenes are highly unsaturated compounds. Ozonation of these compounds results in the addition of three oxygen atoms at each site of unsaturation. In addition, terpene ozonides appear to have significant unexpected pharmacological properties that are different in kind or quality from those of unrelated ozonides disclosed in the prior art.

The toxicity of the terpene ozonides appears to be surprisingly low in systemic use. Our preliminary data suggest that the $LD_{50}$ for a representative compound, linalool ozonide, appears to be greater than about 5000 mg/kg in mice. Furthermore, we have discovered that the irritability of the terpene ozonides is surprisingly low in skin and eye tissues of the rabbit. It is believed that irritability of the compounds in humans is also surprisingly low when used in accordance with the methods of the preferred embodiments.

These ozonides can be used effectively in the generation of superoxide radical, both in and vivo. When the ozonide is combined with an aqueous system, gradual decomposition of the ozonide trioxolane ring structure occurs, with release of superoxide radical Thus, the present invention includes a method for generating superoxide by combining these ozonides with a water-containing system. For example, superoxide production is believed to occur when the compounds are administered to an organism, as well as when the compounds are mixed (with or without a surfactant) into a material that contains water. While the inventor does not wish to be limited to any particular theory of operation, it is believed that at least some of the beneficial and therapeutic properties of these ozonides are due to superoxide generation.

We have also discovered that terpene ozonides, injected in suitable pharmacological compositions, are effective for treatment of systemic viral infections. The present invention includes systemic and localized injection of terpene ozonides, including intravascular, intramuscular, subcutaneous, intraperitoneal, and other injection techniques. In addition, oral administration is also contemplated, preferably in a capsule or other nonaqueous vehicle or system.

In the method of a preferred embodiment, pharmaceutical compositions for systemic use such as for intravenous, intramuscular, or intraperitoneal injection may contain from about 0.01% to about 99% active ingredient, by weight. More preferred injectable compositions contain from about 0.05% to about 45% active ingredient, by weight. Moreover, pharmaceutical compositions for local application in the form of nosedrops or nasal sprays, inhalants, throat sprays, eardrops, ophthalmic ointments or drops, rectal or vaginal suppositories, or ointments or creams for topical applications may contain from about 0.01% to 99.9% active ingredient, by weight. More preferred compositions for local application contain from about 0.05% to 50% active ingredient, by weight.

Pharmaceutical compositions of preferred embodiments may contain from about 0.1% to 99.99% carrier ingredients. The carriers are preferably non-aqueous, because the presence of water rapidly leads to the degradation of the pharmacologically active ozonide compounds used in the preferred embodiment. The carriers employed in pharmaceutical compositions for systemic use are, in addition, preferably injectable or orally ingestible. Nonaqueous, injectable carriers for pharmaceutical compositions of the preferred embodiment for systemic application preferably include: isopropyl myristate, polyethylene glycol or polypropylene glycol (in liquid form), and DMSO, more preferably polyethylene glycol having a molecular weight between about 150 and 1500, most preferably about 600. Good results have been realized, for example, by combining about 4 parts by weight of geraniol ozonide with about 3 parts by weight polyethylene glycol (m.w. 600). This material is storage stable, and can be formulated into an injectable material by combining one part with three parts sterile saline immediately before use. (Although some superoxide production appears to begin immediately upon such combination, no significant degradation of the ozonide is believed to occur within, say, 5 minutes before the material is injected.) Another suitable vehicle is epal, comprising roughly equivalent parts of substantially anhydrous tetradecanol and dodecanol. Non-aqueous carriers suitable for pharmaceutical compositions for local application in accordance with the methods of the preferred embodiment include: DMSO, hydrogenated vegetable oil, mineral oil, carbomer 934, glycerin, propylene glycol, propyl paraben, polysorbate 60, glyceryl stearate, ethanol, and modified food starch.

Therapeutic dosages of the terpene ozonides when used for systemic injection in accordance with the methods of the preferred embodiments are preferably in the range of 1 mg to 10 g active ingredient for a 70 kg adult one time per day, more preferably in the range of 10 mg to 1 g active ingredient for a 70 kg adult one time per day, and most preferably in the range of 20 mg to 500 mg active ingredient for a 70 kg adult one or two times per day. Therapeutic dosages of the terpene ozonides when used for topical application in the form of creams, ointments, or rectal or vaginal suppositories in accordance with the methods of the preferred embodiments are preferably in the range of 100 g to 10 g used one to four times per day for each $cm^2$ of affected area, more preferably 1 mg to 1 g used one to four times per day for each $cm^2$ of affected area, and most preferably 5 mg to 200 g used one to four times per day for each $cm^2$ of affected area. Therapeutic dosages of the terpene ozonides for use in other methods of local application in accordance with the preferred embodiments, such as nosedrops or nasal sprays, inhalants, throat sprays, eardrops, or ophthalmic ointments or drops are preferably in the range of 100 g to 1 g per application used one to four times per day, and more preferably 1 mg to 100 mg per application used one to four times per day.

Oral compositions may be given at the same dosage as the injectable compositions, or may be given at up to twice the injection dosage.

We have discovered that intramuscular injection of a terpene ozonide in a pharmaceutically acceptable carrier, with or without contemporaneous oral administration, is effective in treating the symptoms of AIDS. A patient receiving this treatment gets fewer of the opportunistic infections common in AIDS patients. Such a patient also feels less lethargic and has a generally improved sense of physical well-being. This improvement in symptoms has been shown to be the result of a restoration of normal T4-cell levels after injection with the terpene ozonide. The restoration is believed to be the result of an antiviral effect of the terpene ozonide.

It is believed that treatment of persons infected with HIV who do not yet express symptoms of AIDS can be effectively treated with systemic injections of terpene ozonides, for example in the manner of Example 11, in order to prevent the appearance of the symptoms of AIDS.

Furthermore, it is believed that administration of terpene ozonides in accordance with the present invention will be beneficial in the treatment of immune disorders other than AIDS. It is believed that systemic injection of the terpene ozonides will restore a normal level of T4-cells in many immunocompromised patients, including patients on immunosuppressive therapy, chemotherapy, or radio-therapy, and patients with congenital immunodeficiencies. Lupus and rheumatoid arthritis also respond to therapy with the terpene ozonides of the present invention. In a preferred embodiment, restoration of T4-cell levels is accomplished by systemic injection of terpene ozonides in the manner of Example 11.

It is also believed that treatment of blood products with a terpene ozonide of the present invention prior to its medical use, will eliminate HIV and any other viral activity present in the blood. From about 0.5 to about 10 mg/liter of terpene ozonide can be used in treating blood in, for example, a blood bank.

The terpene ozonides seem to be effective not only against HIV infection. They also appear to be effective in the treatment of other retroviral infections, such as Herpes lesions, including chicken pox, EBV infection, or CMV infection. Systemic injection of terpene ozonides is believed to be effective in treatment of these other retroviral infections. Additionally, topical application of the terpene ozonides in pharmacologically effective compositions is believed to be effective in the treatment of lesions of these retroviral infections. Moreover, it is believed that the terpene ozonides will be effective against many disparate viral infections, including viral infections of non-retroviral origin. In this regard, it is believed that systemic injection of a terpene ozonide in a pharmacologically acceptable carrier or excipient is effective in the treatment of systemic infections caused by non-retroviral viruses, including Epstein Barr Virus, most of the enteroviruses, reoviruses, rhabdoviruses (including rabies), arboviruses, and arenaviruses. It is also believed that intra-vaginal application of a terpene ozonide in a pharmaceutically acceptable carrier or excipient is effective against condylomata acuminata, molluscum contagiousum, and other viral infections of the vagina. Also in this regard, it is believed that topical application of a terpene ozonide in pharmacologically acceptable carrier or excipient is non-irritating and effective in the treatment of common warts and other viral lesions of the skin. Further in this regard, it is believed that application of a terpene ozonide in a pharmacologically acceptable carrier or excipient in the form of nosedrops or nasal sprays, inhalants, throat sprays, eardrops, ophthalmic ointments or drops, is effective in the treatment of viral infections of the eye, ear, nose, and throat, including upper respiratory infections of viral origin such as colds and flu. Finally, they appear to be useful in treatment of rheumatoid arthritis, which may be caused by a viral pathogen, as well as useful in treatment of other autoimmune disorders.

For example, in treating the common cold, an aerosol mist containing 2 ml of the nasal inhalant of Example 10 may be sprayed onto each nostril of a patient suffering from the common cold. The process is repeated every four hours. Within one hour of the first treatment, the patient will generally report easier breathing through the nose. With two days of treatments, the patient can usually breathe easily through both nostrils and reports no sore throat.

EXAMPLE 1

Preparation of squalene ozonide

Squalene is ozonized by preparing a solution of 10 g squalene in 100 ml hexane. Ozone gas (4% in oxygen, from a corona discharge ozone generator), is bubbled through this solution via a glass sparger at the rate of 5000 cc/min. The reaction is exothermic, and the reaction temperature is kept within the range of 0° C. to 35° C., preferably 20° C. to 25° C., and more preferably, 22° C. to 24° C., using a cool water bath. The resulting product is the ozonide of beta carotene, and has a 98% weight gain over squalene.

EXAMPLE 2

Preparation of linalool ozonide

The ozonide of linalool is prepared by bubbling ozone (4% in oxygen, from a corona discharge ozone generator) through 100 ml neat linalool via a glass sparger. The reaction is exothermic, and the reaction temperature is kept within the range of 0° C. to 35° C., preferably 20° C. to 25° C., and more preferably, 22° C. to 24° C., using a cool water bath. The resulting product is the ozonide of linalool, and has a 31% weight gain over linalool.

EXAMPLE 3

Preparation of Geraniol Ozonide

The ozonide of linalyl acetate was prepared by bubbling ozone (4% in oxygen, from a corona discharge ozone generator) through 5 ml neat geraniol at the rate of 5000 cc/min. The reaction mixture was cooled in a water bath, and after 20 minutes, the evolution of heat ceased, indicating completion of the ozonation process. The resulting material had no odor, and was soluble in polyethylene glycol (600 m.w.), isopropyl myristate, and mineral oil.

EXAMPLE 4

Primary skin irritation test of ozonide of linalool

Six healthy New Zealand White rabbits were tested for skin irritation. Approximately four hours prior to application of the ozonide sample, the backs of the animals were clipped free of fur. Each rabbit received epidermal abrasions with a sterile needle at one test site while the skin at another test site remained intact. A 1.0% solution of linalool ozonide in isopropyl myristate was prepared A 0.5 ml portion of the test solution was applied to each site by introduction under a double gauze layer to an area of skin approximately 1" square. The patches were covered with a nonreactive tape and the entire test site was wrapped with a binder. After 24 hours, the binders, tape, test material residue was removed with 70% isopropyl alcohol. An evaluation was also made at 72 hours after application. The reactions were scored according to the methods described in the Federal Hazardous Substances Act. The test solution had a Primary Irritation Index (PII) of 1.0. According to FHSA regulations, a material with a PII of less than 5.00 is generally not considered a primary irritant to the skin.

EXAMPLE 5

Ocular irritation test in the rabbit of the ozonide of linalool

Six healthy New Zealand White rabbits were selected for study. The rabbits' eyes were judged free of irritation prior to the study by examining with a pen light and under UV light after installation of 2% fluorescein stain. A 1% solution of the ozonide of linalool was prepared in isopropyl myristate. A 0.1 ml portion of this test solution was instilled into the lower conjunctival sac of one eye of each rabbit. The lids were held closed for one second. The opposite eye of each rabbit received 0.1 ml of the isopropyl myristate, as control. At 24, 48, and 72 hours post dosing, the eyes were examined with a pen light and re-examined with UV light following fluorescein staining of the cornea. Under the conditions of this test, the test solution was considered a non-irritant to ocular tissue of the rabbit.

EXAMPLE 6

An injectable composition for use in treatment of AIDS

| | |
|---|---|
| 250 mg/ml | ozonide of geraniol from Example 3 |
| balance | oil/water emulsion (soybean) with 0.1% lecithin |

EXAMPLE 7

A vaginal suppository for treatment of condylomata acuminata

| | |
|---|---|
| 2% w/v | Ozonide of geraniol from Example 3 |
| Balance | Hydrogenated vegetable oil base |

EXAMPLE 8

| | |
|---|---|
| 1% w/v | Ozonide of linalool |
| 60% w/v | Carbomer 934 |
| 1% w/v | Disodium edetate |
| 10% w/v | Glycerin |
| Balance | propylene glycol, 600 m.w. |

EXAMPLE 9

A topical cream effective against chicken pox, herpes simplex and other viral lesions

| | |
|---|---|
| 2.5% w/v | Ozonide of linalool |
| 48% w/v | Propylene glycol |
| 30% w/v | Propyl paraben |
| 5% w/v | Polysorbate 60 |
| 10% w/v | Glyceryl monostearate |
| Balance | Mineral oil |

EXAMPLE 10

A nasal inhalant effective against upper respiratory infections

| 1 mg/ml | ozonide of citral |
| balance | epal |

EXAMPLE 11

Test of restoration of immune cell levels in an AIDS patient

A patient testing positive for the presence of HIV antibodies and diagnosed with AIDS was variously treated with the composition of Example 6 for a period of 99 days. On days 0 through 6, the patient received daily intravenous injections of 4.0 ml of the composition of Example 6. On days 7 to 19, the patient gas treated a.q.i.v. with the same composition. From days 20 through 44, the patient received no treatment. The patient received daily intramuscular injections from days 45 through 77. An immunodeficiency screening was performed on days 7, 20, 45, and 78. The results, expresses in cells/cmm, are shown in Table 2.

TABLE 2

|  | Day 0 | Day 7 | Day 20 | Day 45 | Day 78 |
| --- | --- | --- | --- | --- | --- |
| Total WBC | 3700 | 4300 | 6600 | 4900 | 5300 |
| Total lymphs | 1005 | 2182 | 2406 | 1633 | 1296 |
| Total T lymphs | 834 | 1724 | 2213 | 1486 | 1102 |
| Supp-Cytox T8 | 381 | 851 | 914 | 702 | 635 |
| Help-Inducer T4 | 392 | 873 | 1155 | 702 | 414 |

The results show that intra-venous injection of the composition of Example 6 increased the levels of all types of cells screened. These cell levels decreased during the period of no treatment, and remained relatively stable during the period of intra-muscular treatment.

It is believed that intra-venous systemic injection in the manner described in Example 11 is effective in the treatment of other viral infections as well.

EXAMPLE 12

In vitro anti-viral assay of the ozonide of linalool

A culture of SV-40 is grown in African Green Monkey (AGM) cells. The culture is harvested in sterile saline. The titer of SV-40 in the suspension is determined by Standard Plate Count Method in AGM cells. A working suspension of SV-40 with a titer of approximately $1.0 \times 10^7$ plaque forming units (PFUs)/0.1 ml is then prepared. Four aliquots of 1 ml each of test solution containing 2.0% ozonide of linalool are removed and placed in separate sterile screw-capped tubes. Each sample is inoculated with 0.1 ml of the working suspension of SV-40 to yield a final concentration of approximately $1 \times 10^6$ PFUs/1 ml of the product. The samples are stored at 20°–25° C. for a total of 28 days. Samples are selected at 7 day intervals to determine the number of viable PFUs present. A control with uninoculated solution is also stored with samples selected at the same intervals. At 7 days, and all subsequent sample selections, there are less than 10 PFUs present. No PFUs are present in any control sample.

EXAMPLE 13

Preparation of blood products free of viral activity

Blood obtained from a donor is mixed with 0.5 g of ozonide of geraniol from Example 3 per unit (500 ml) of blood. The blood is then processed in the normal manner. The resulting blood products are free of detectable HIV or other viral activity using standard viral assays.

EXAMPLE 14

Test for efficacy of treatment of chicken pox

A small dose (approximately 25 l) of the composition of Example 9 is topically applied to each lesion on the left side of a child suffering from chicken pox. Lesions on the right side are treated with the composition lacking in active ingredient. Within 24 hours, the lesions on the child's left side are significantly reduced with little or no self-induced trauma from scratching. The lesions on the child's right side are unchanged in size, and show the effects of trauma from scratching.

In a manner similar to that employed in Example 15, other viral lesions, such as common warts and herpes lesions may be treated by topical application of a terpene ozonide in a pharmaceutically acceptable carrier or excipient.

EXAMPLE 15

Test for efficacy of treatment of condylomata acuminata

A 5 ml suppository with the composition of Example 4 is administered intra-vaginally to one group of patients suffering from condylomata acuminata. A second group of such patients receive a suppository without the active ingredient of Example 4. A third group receives cryogenic treatment of the affected area, a commonly used treatment for condylomata acuminata. The average size of the lesions in each group is approximately 2 $cm^2$. Within seven days, the patients of the first group have reduced reddening of the vagina and within 15 days, colposcopy does not reveal papilloma viruses. In the second group of patients, the lesions are unchanged after 15 days. Patients in the third group have no condylomata lesions immediately after treatment, however, these patients continue to complain of pain and bleeding for up to 30 days after the procedure is performed.

EXAMPLE 16

Treatment of Rheumatoid Arthritis

It has been theorized that rheumatoid arthritis is caused by a viral agent. The antiviral ozonides of the present invention are believed to be efficacious in treatment of this disease. Thus, a 20% oral preparation comprising capsules containing citral ozonide in medium chain triglyceride (MCT) is prepared and is taken twice daily by a patient suffering from rheumatoid arthritis. Each dose delivers 400 mg active ingredient to the 60 kg patient. After 1 week, the ANA of the patient has dropped from approximately 2500 to 100, indicating remission of the disease. Similar treatment is effective against psoriasis.

I claim:

1. A method for treating viral infections of HIV in a mammal, comprising the parenteral application of a pharmacologically antiviral effective amount of an ozonide of a terpene in a pharmaceutically acceptable carrier or excipient.

2. The method of claim 1, wherein said terpene is selected from the group consisting of: limonene, citronella, alpha-carotene, beta-carotene, vitamin A, linalool, linalyl acetate, squalene, geraniol, alpha-pinene, loganin, cymene, farnesanes, eudesmanes, acoranes, cedranes, chamigranes, caryophyllanes, illudanes, humulenes, himachalenes, longifolanes, perhydroazulenes, quaianes, quaianolides, germacranes, labdane, clerodanes, abietic acid, phyllocladene, giberellins, ophiobolin A, retigeranic acid, gasgardic acid, lanosterol, euphol, oleanane, ursane, lupeol, hydroxyhopanone, lupanes, hopanes, B-selinene, zingibene, camphene, sabinene, ocimene, myrcene, nerol, citral A, citral B, farnesol, bisabolene, phytol and cecropia juvenile hormone.

3. The method of claim 1, wherein said terpene is a hemi-terpene, mono-terpene, sesqui-terpene, di-terpene, ses-terpene, tri-terpene, or tetra-terpene.

4. The method of claim 1, wherein said viral infection is systemic, said parenteral application is by systemic injection, and said composition is for systemic injection, and comprises an injectable non-aqueous carrier.

5. The method of claim 1, wherein said viral infection produces local sites of infection.

6. The method of claim 5, wherein said viral infection is an upper respiratory infection.

7. The method of claim 5, wherein said viral infection is an infection of the eye, ear, nose, or throat.

8. A method of treating mammalian blood to be used for medical applications in the treatment of HIV comprising the addition of an azonide of a hemi-terpene, mono-terpene, sesqui-terpene, di-terpene, ses-terpene, tri-terpene, or tetra-terpene to said blood causing said blood to be free of viral activity.

* * * * *